(12) United States Patent
Goldman

(10) Patent No.: US 9,198,840 B1
(45) Date of Patent: Dec. 1, 2015

(54) USE OF COOLING AGENT TO IMPROVE COSMETICS

(71) Applicant: Skindinavia, Inc., Chestnut Hill, MA (US)

(72) Inventor: Allen S. Goldman, Chestnut Hill, MA (US)

(73) Assignee: Skindinavia, Inc., Scottsdale, AZ (US)

( * ) Notice: Subject to any disclaimer, the term of this patent is extended or adjusted under 35 U.S.C. 154(b) by 0 days.

(21) Appl. No.: 13/969,872

(22) Filed: Aug. 19, 2013

Related U.S. Application Data

(63) Continuation-in-part of application No. 13/705,776, filed on Dec. 5, 2012, now abandoned, which is a continuation of application No. 13/009,536, filed on Jan. 19, 2011, now Pat. No. 8,329,145.

(60) Provisional application No. 61/345,727, filed on May 18, 2010, provisional application No. 61/422,433, filed on Dec. 13, 2010.

(51) Int. Cl.
*A61K 8/11* (2006.01)
*A61K 8/37* (2006.01)
*A61Q 1/02* (2006.01)

(52) U.S. Cl.
CPC .... *A61K 8/11* (2013.01); *A61Q 1/02* (2013.01)

(58) Field of Classification Search
None
See application file for complete search history.

(56) References Cited

U.S. PATENT DOCUMENTS 8,003,615 B2 8/2011 Sakamoto et al.
8,329,145 B1 * 12/2012 Goldman ........................ 424/43
2004/0136916 A1 * 7/2004 Garrison ........................ 424/45
2006/0110353 A1 * 5/2006 Rollat-Corvol et al. ... 424/70.17

OTHER PUBLICATIONS

Label from a product on sale in Jan. 2007.

* cited by examiner

*Primary Examiner* — Jyothsna Venkat
(74) *Attorney, Agent, or Firm* — Pandiscio & Pandiscio

(57) ABSTRACT

A pumpable liquid spray formulation for retarding degradation of color cosmetics, the pumpable liquid spray formulation being characterized by:
the presence of at least one encapsulated evaporative cooling agent; and
at least one entrained solvent;
and the absence of fluorocarbon-based evaporative cooling agents,
whereby the reduction of the surface temperature of the color cosmetics is achieved by a controlled release of the entrained solvents by the at least one encapsulated evaporative cooling agent.

14 Claims, No Drawings

USE OF COOLING AGENT TO IMPROVE COSMETICS

REFERENCE TO PENDING PRIOR PATENT APPLICATIONS

This patent application is a continuation-in-part of prior U.S. patent application Ser. No. 13/705,776, filed Dec. 5, 2012 by Skindinavia, Inc. for USE OF COOLING AGENT TO IMPROVE COSMETICS, which is a continuation of prior U.S. patent application Ser. No. 13/009,536, filed Jan. 19, 2011 by Allen S. Goldman for USE OF COOLING AGENT TO IMPROVE COSMETICS, which in turn claims benefit of: (i) prior U.S. Provisional Patent Application Ser. No. 61/345,727, filed May 18, 2010 by Allen Goldman for USE OF COOLING FLUID TO EXTEND MAKEUP WEAR, LUMINOSITY, AND MOISTURIZATION, AND TO REDUCE SURFACE SHINE; and (ii) prior U.S. Provisional Patent Application Ser. No. 61/422,433, filed Dec. 13, 2010 by Allen S. Goldman for USE OF COOLING AGENT TO IMPROVE COSMETICS AND OTHER SKIN-APPLIED PRODUCTS.

The four (4) above-identified patent applications are hereby incorporated herein by reference.

FIELD OF THE INVENTION

This invention relates to cosmetics in general, and more particularly to the use of a cooling agent to improve cosmetics.

BACKGROUND OF THE INVENTION

Color cosmetics are used to enhance facial appearance and cover facial imperfections. Examples of such color cosmetics include, but are not limited to, foundation, eye shadow, blush, and concealer.

Color cosmetics typically degrade over time. The rate of degradation can be influenced by a number of factors including, but not limited to, ingredient characteristics, user skin type, skin temperature, the temperature of the surrounding environment, humidity of the surrounding environment, etc. Since such degradation undermines the appearance of the color cosmetics, it is generally desirable that the color cosmetics resist such degradation.

To this end, a number of color cosmetic manufacturers have created "extended wear" products (e.g., foundations, mascaras, eye shadows, etc.). However, many users find these extended wear products to be only partially satisfactory, since (i) they are typically available in only a limited range of colors and shades, (ii) they are generally difficult to remove, and (iii) they typically have an unnatural "feel" (i.e., the extended wear products generally do not offer the same "lightweight" feel that standard color cosmetics offer).

Alternatively, users may also use a "make-up setting spray" to extend the wear of their color cosmetics. Such make-up setting sprays are applied as a surface layer over the color cosmetics and act as a protective coating to help prevent degradation of the color cosmetics. However, such make-up setting sprays tend to stiffen the make-up, which can result in user discomfort. Furthermore, such make-up setting sprays typically comprise polymers (e.g., acrylics) dissolved in a solvent (e.g., alcohol), which produces a clear, lacquer-like coating on the make-up, which can appear unnatural and feel uncomfortable. In addition, some people find that the solvent (e.g., alcohol) used in these make-up setting sprays can be an irritant to their skin.

Thus there is a need for a new way to extend the wear of make-up which does not suffer from the aforementioned limitations of the prior art.

SUMMARY OF THE INVENTION

The present invention provides a new way to extend the wear of make-up which does not suffer from the aforementioned limitations of the prior art.

More particularly, the present invention comprises the provision and use of a novel pumpable liquid spray formulation which is sprayed over the color cosmetics, after the color cosmetics have been applied to the skin, so as to retard degradation of the color cosmetics and thereby extend make-up wear. This novel formulation may comprise a suspension containing, among other things, a novel cooling agent. The novel cooling agent comprises a volatile component which slowly evaporates during use, thereby providing "evaporative cooling" to the color cosmetics. This evaporative cooling significantly reduces the rate at which moisture and/or other volatiles migrate out of the color cosmetics, thereby significantly extending the useful life of the color cosmetics.

In one preferred form of the present invention, the novel cooling agent comprises a volatile hydroether (e.g., methyl perfluorobutyl ether and methyl perfluoroisobutyl ether), either alone or in combination with a carrier (e.g., polyhydroxystearic acid) which serves to deliver the volatile hydroether to the color cosmetics. The volatile hydroether (i.e., the novel cooling agent) can be contained in, and delivered by, microcapsules which, when ruptured, release the volatile hydroether. In essence, as water in the spray starts to evaporate, the carrier (e.g., the polyhydroxystearic acid) starts to give up the volatile hydroether (e.g., methyl perfluorobutyl ether and methyl perfluoroisobutyl ether).

If desired, the methyl perfluorobutyl ether and/or methyl perfluoroisobutyl ether can be replaced by perfluoroisohexane, perfluoro poly ether and/or hydro fluoro poly ether.

In one preferred manner of use, the color cosmetics are applied to the skin of the user; and then the pumpable liquid spray formulation is applied to the color cosmetics as a fine mist while the color cosmetics are on the skin of the user.

In one preferred form of the invention, there is provided a pumpable liquid spray formulation for retarding degradation of color cosmetics, the pumpable liquid spray formulation comprising:

water, 82.228% by weight;
alcohol denat, 9.0% by weight;
polyhydroxystearic acid, 2.23% by weight;
pvp, 2.0% by weight;
methyl perfluorobutyl ether, 1.25% by weight;
methyl perfluoroisobutyl ether, 1.25% by weight;
dimethicone peg-7 phosphate, 0.75% by weight;
ppg-3 benzyl ether myristate, 0.5% by weight;
caprylyl glycol, 0.5% by weight;
methyl methacrylate cross polymer, 0.12% by weight;
sodium hydroxide, 0.07% by weight;
sodium cocamidopropyl pg dimonium chloride phosphate, 0.05% by weight;
glycereth-5 lactate, 0.01% by weight;
N,2,3-trimethyl-2-isopropyl butamide, 0.01% by weight;
ethylhexyl isononanoate, 0.01% by weight;
isononyl isononanoate, 0.01% by weight;
fragrance, 0.01% by weight;
aloe barbandensis leaf extract, 0.001% by weight; and
poloxamer 407, 0.001% by weight;
wherein all of the foregoing percentage weights have a tolerance band of ±4% of their stated value.

In another preferred form of the invention, there is provided a method for improving cosmetic wear, the method comprising:
providing a pumpable liquid spray formulation for retarding degradation of color cosmetics, the pumpable liquid spray formulation comprising:
water, 82.228% by weight;
alcohol denat, 9.0% by weight;
polyhydroxystearic acid, 2.23% by weight;
pvp, 2.0% by weight;
methyl perfluorobutyl ether, 1.25% by weight;
methyl perfluoroisobutyl ether, 1.25% by weight;
dimethicone peg-7 phosphate, 0.75% by weight;
ppg-3 benzyl ether myristate, 0.5% by weight;
caprylyl glycol, 0.5% by weight;
methyl methacrylate cross polymer, 0.12% by weight;
sodium hydroxide, 0.07% by weight;
sodium cocamidopropyl pg dimonium chloride phosphate, 0.05% by weight;
glycereth-5 lactate, 0.01% by weight;
N,2,3-trimethyl-2-isopropyl butamide, 0.01% by weight;
ethylhexyl isononanoate, 0.01% by weight;
isononyl isononanoate, 0.01% by weight;
fragrance, 0.01% by weight;
aloe barbandensis leaf extract, 0.001% by weight; and
poloxamer 407, 0.001% by weight;
wherein all of the foregoing percentage weights have a tolerance band of ±4% of their stated value;
applying color cosmetics to the skin of the user; and
applying the pumpable liquid spray formulation to the color cosmetics, as an aerosol mist while the color cosmetics are on the skin of the user.

In another preferred form of the invention, there is provided a method for improving cosmetic wear, the method comprising:
providing a pumpable liquid spray formulation for retarding degradation of color cosmetics, the pumpable liquid spray formulation comprising:
water, 82.228% by weight;
alcohol denat, 9.0% by weight;
polyhydroxystearic acid, 2.23% by weight;
pvp, 2.0% by weight;
methyl perfluorobutyl ether, 1.25% by weight;
methyl perfluoroisobutyl ether, 1.25% by weight;
dimethicone peg-7 phosphate, 0.75% by weight;
ppg-3 benzyl ether myristate, 0.5% by weight;
caprylyl glycol, 0.5% by weight;
methyl methacrylate cross polymer, 0.12% by weight;
sodium hydroxide, 0.07% by weight;
sodium cocamidopropyl pg dimonium chloride phosphate, 0.05% by weight;
glycereth-5 lactate, 0.01% by weight;
N,2,3-trimethyl-2-isopropyl butamide, 0.01% by weight;
ethylhexyl isononanoate, 0.01% by weight;
isononyl isononanoate, 0.01% by weight;
fragrance, 0.01% by weight;
aloe barbandensis leaf extract, 0.001% by weight; and
poloxamer 407, 0.001% by weight;
wherein all of the foregoing percentage weights have a tolerance band of ±4% of their stated value;
applying the pumpable liquid spray formulation to the skin of the user as an aerosol mist; and
applying color cosmetics to the skin of the user over the pumpable liquid spray formulation.

In another preferred form of the invention, there is provided a pumpable liquid spray formulation for retarding degradation of color cosmetics, the pumpable liquid spray formulation comprising:
water, 82.228% by weight;
alcohol denat, 9.0% by weight;
polyhydroxystearic acid, 2.23% by weight;
pvp, 2.0% by weight;
perfluoroisohexane, 2.5% by weight;
dimethicone peg-7 phosphate, 0.75% by weight;
ppg-3 benzyl ether myristate, 0.5% by weight;
caprylyl glycol, 0.5% by weight;
methyl methacrylate cross polymer, 0.12% by weight;
sodium hydroxide, 0.07% by weight;
sodium cocamidopropyl pg dimonium chloride phosphate, 0.05% by weight;
glycereth-5 lactate, 0.01% by weight;
N,2,3-trimethyl-2-isopropyl butamide, 0.01% by weight;
ethylhexyl isononanoate, 0.01% by weight;
isononyl isononanoate, 0.01% by weight;
fragrance, 0.01% by weight;
aloe barbandensis leaf extract, 0.001% by weight; and
poloxamer 407, 0.001% by weight;
wherein all of the foregoing percentage weights have a tolerance band of ±4% of their stated value.

In another preferred form of the invention, there is provided a method for improving cosmetic wear, the method comprising:
providing a pumpable liquid spray formulation for retarding degradation of color cosmetics, the pumpable liquid spray formulation comprising:
water, 82.228% by weight;
alcohol denat, 9.0% by weight;
polyhydroxystearic acid, 2.23% by weight;
pvp, 2.0% by weight;
perfluoroisohexane, 2.5% by weight;
dimethicone peg-7 phosphate, 0.75% by weight;
ppg-3 benzyl ether myristate, 0.5% by weight;
caprylyl glycol, 0.5% by weight;
methyl methacrylate cross polymer, 0.12% by weight;
sodium hydroxide, 0.07% by weight;
sodium cocamidopropyl pg dimonium chloride phosphate, 0.05% by weight;
glycereth-5 lactate, 0.01% by weight;
N,2,3-trimethyl-2-isopropyl butamide, 0.01% by weight;
ethylhexyl isononanoate, 0.01% by weight;
isononyl isononanoate, 0.01% by weight;
fragrance, 0.01% by weight;
aloe barbandensis leaf extract, 0.001% by weight; and
poloxamer 407, 0.001% by weight;
wherein all of the foregoing percentage weights have a tolerance band of ±4% of their stated value;
applying color cosmetics to the skin of the user; and
applying the pumpable liquid spray formulation to the color cosmetics, as an aerosol mist while the color cosmetics are on the skin of the user.

In another preferred form of the invention, there is provided a method for improving cosmetic wear, the method comprising:
providing a pumpable liquid spray formulation for retarding degradation of color cosmetics, the pumpable liquid spray formulation comprising:
water, 82.228% by weight;
alcohol denat, 9.0% by weight;
polyhydroxystearic acid, 2.23% by weight;
pvp, 2.0% by weight;
perfluoroisohexane, 2.5% by weight;

dimethicone peg-7 phosphate, 0.75% by weight;
ppg-3 benzyl ether myristate, 0.5% by weight;
caprylyl glycol, 0.5% by weight;
methyl methacrylate cross polymer, 0.12% by weight;
sodium hydroxide, 0.07% by weight;
sodium cocamidopropyl pg dimonium chloride phosphate, 0.05% by weight;
glycereth-5 lactate, 0.01% by weight;
N,2,3-trimethyl-2-isopropyl butamide, 0.01% by weight;
ethylhexyl isononanoate, 0.01% by weight;
isononyl isononanoate, 0.01% by weight;
fragrance, 0.01% by weight;
aloe barbandensis leaf extract, 0.001% by weight; and
poloxamer 407, 0.001% by weight;
wherein all of the foregoing percentage weights have a tolerance band of ±4% of their stated value;
applying the pumpable liquid spray formulation to the skin of the user as an aerosol mist; and
applying color cosmetics to the skin of the user over the pumpable liquid spray formulation.

In another preferred form of the invention, there is provided a pumpable liquid spray formulation for retarding degradation of color cosmetics, the pumpable liquid spray formulation being characterized by:
the presence of at least one encapsulated evaporative cooling agent; and
at least one entrained solvent;
and the absence of fluorocarbon-based evaporative cooling agents,
whereby the reduction of the surface temperature of the color cosmetics is achieved by a controlled release of the entrained solvents by the at least one encapsulated evaporative cooling agent.

In another preferred form of the invention, there is provided a method for improving cosmetic wear, the method comprising:
providing a pumpable liquid spray formulation for retarding degradation of color cosmetics, the pumpable liquid spray formulation being characterized by:
the presence of at least one encapsulated evaporative cooling agent; and
at least one entrained solvent;
and the absence of fluorocarbon-based evaporative cooling agents,
whereby the reduction of the surface temperature of the color cosmetics is achieved by a controlled and slow release of the entrained solvents by the at least one encapsulated evaporative cooling agent;
applying color cosmetics to the skin of the user; and
applying the pumpable liquid spray formulation to the color cosmetics, as a fine mist while the color cosmetics are on the skin of the user.

In another preferred form of the invention, there is provided a method for improving cosmetic wear, the method comprising:
providing a pumpable liquid spray formulation for retarding degradation of color cosmetics, the pumpable liquid spray formulation being characterized by:
the presence of at least one encapsulated evaporative cooling agent; and
at least one entrained solvent;
and the absence of fluorocarbon-based evaporative cooling agents,
whereby the reduction of the surface temperature of the color cosmetics is achieved by a controlled release of the entrained solvents by the at least one encapsulated evaporative cooling agent;
applying the pumpable liquid spray formulation to the skin of the user as a fine mist; and
applying color cosmetics to the skin of the user over the pumpable liquid spray formulation.

DETAILED DESCRIPTION OF THE INVENTION

The present invention provides a new way to extend the wear of make-up which does not suffer from the aforementioned limitations of the prior art.

More particularly, the present invention comprises the provision and use of a novel pumpable liquid spray formulation which is sprayed over the color cosmetics, after the color cosmetics have been applied to the skin, so as to retard degradation of the color cosmetics and thereby extend make-up wear. This novel formulation may comprise a suspension containing, among other things, a novel cooling agent. The novel cooling agent comprises a volatile component which slowly evaporates during use, thereby providing "evaporative cooling" to the color cosmetics. This evaporative cooling significantly reduces the rate at which moisture and/or other volatiles migrate out of the color cosmetics, thereby significantly extending the useful life of the color cosmetics.

In one preferred form of the invention, the novel cooling agent comprises a volatile hydroether (e.g., methyl perfluorobutyl ether and methyl perfluoroisobutyl ether), either alone or in combination with a carrier (e.g., polyhydroxystearic acid) which serves to deliver the volatile hydroether to the color cosmetics. The volatile hydroether (i.e., the novel cooling agent) can be contained in, and delivered by, microcapsules which, when ruptured, release the volatile hydroether. In essence, as water in the spray starts to evaporate, the carrier (e.g., the polyhydroxystearic acid) starts to give up the volatile hydroether (e.g., methyl perfluorobutyl ether and methyl perfluoroisobutyl ether).

If desired, the methyl perfluorobutyl ether and/or methyl perfluoroisobutyl ether can be replaced by perfluoroisohexane, perfluoro poly ether and/or hydro fluoro poly ether.

In one preferred manner of use, the color cosmetics are applied to the skin of the user; and then the pumpable liquid spray formulation is applied to the color cosmetics as a fine mist while the color cosmetics are on the skin of the user.

Table I provides one preferred formulation for the novel pumpable liquid spray formulation of the present invention, wherein all of the percentage weights provided in Table I have a tolerance band of ±4% of their stated value. This pumpable liquid spray formulation comprises a suspension and has been found to provide an excellent "general purpose" cosmetic enhancer, particularly well-suited for "normal" skin types.

The specific purpose and benefits associated with each of the ingredients incorporated in the novel pumpable liquid spray formulation of the present invention are provided in Table I.

The following additional comments are made with respect to the ingredients incorporated in the novel pumpable liquid spray formulation of the present invention:
with respect to "water", water is a carrier of the technology, the more water used the finer and lighter the mist—it has been discovered that, for successful spray application, it is important that water constitute at least 82% (by weight) of the pumpable liquid spray formulation of the present invention;
with respect to "alcohol denat" (i.e., de-natured alcohol), this is preferably SDA Alcohol 40B 190 Proof;
the polyhydroxystearic acid is an encapsulating agent, the microcapsules release the cooling agent, if the cooling agent were not encapsulated in the polyhydroxystearic acid, the cooling agent would prematurely evaporate—in other words, the polyhydroxystearic acid comprises a foam burst stabilizer to add longer cooling for longer make-up wear, the polyhydroxystearic acid releases its encapsulated material when removed from an aqueous environment, i.e., when water in the spray evaporates—it has been discovered that, for proper cooling release, it is important that the polyhydroxystearic acid comprise between 0.001%-3.0% (by weight) of the pumpable liquid spray formulation of the present invention;

the PVP (polyvinylpyrrolidone) is kept under a concentration of 3.0% (by weight) in order to provide a more natural look and a less shiny appearance—a lower concentration provides increased sprayability and reduces shine, since this component is a plasticizer and gives a sheen—in the preferred embodiment, the PVP is kept at a concentration of 2.0% by weight;

the methyl perfluorobutyl ether is an active ingredient for longer wear—for proper cooling, this component should comprise more than 1% (by weight) of the pumpable liquid spray formulation of the present invention;

the methyl perflouroisobutyl ether is an active ingredient for longer wear—for proper cooling, this component should comprise more than 1% (by weight) of the pumpable liquid spray formulation of the present invention;

PPG-3 benzyl ether myristate is a varied pigment wetter to keep the make-up from clumping or sliding based on skin type;

caprylyl glycol is a preservative, it is important that this material not be replaced with phenoxyethanol, gluconolactone and/or sodium benzoate since such alternative ingredients have been found to cause irritation to users with sensitive skin;

the methyl methacrylate cross-polymer is an oil absorber and light diffuser, it is extremely important that it be finely ground (e.g., to an average particle size of 4.5-8.5 microns or less) in order to avoid clogging the sprayer which is used to apply the novel formulation to the color cosmetics—the methyl methacrylate cross-polymer is an anti-shine ingredient which may be increased for oily skin types and/or may be decreased for dry skin types, but in any case preferably constitutes less than 0.5% (by weight) of the pumpable liquid spray formulation of the present invention, and most preferably about 0.12% (by weight) of the pumpable liquid spray formulation;

the glycereth-5 lactate is a moisturizer, higher levels may be used for dry or mature skin;

the ethylhexyl isononanoate provides a cooling feature;

the isononyl isononoate provides a cooling feature;

the specific fragrance used can be varied according to customer preference, in one preferred form of the invention, the fragrance is Green Tea for a lighter scent and reduced skin irritation;

aloe barbandensis leaf extract is a moisturizer, higher levels may be used for dry or mature skin; and poloxamer 407 is a thickener and emollient, in practice it has been found that it is extremely important to include this ingredient in the formulation in order keep particulates and solids evenly dispersed within the suspension and prevent any settling out of the finely ground constituent components.

In the preceding embodiments of the present invention, the novel pumpable liquid spray formulation achieves a cooling effect through the use of fluorocarbon-based evaporative cooling agents (i.e., methyl perfluorobutyl ether and methyl perflouroisobutyl ether) and encapsulated evaporative cooling agents (i.e., sodium cocamidopropyl PG dimonium chloride phosphate, ethylhexyl isononanoate and isononyl isononanoate). However it has now been discovered that the performance of the present invention can be further improved through the elimination of the fluorocarbon-based evaporative cooling agents and the use of increased amounts of the encapsulated evaporative cooling agents.

Thus, in another preferred formulation of the novel pumpable liquid spray formulation of the present invention, it has been found that the performance of the invention can be improved (e.g., by significantly extending the effective life or "wear time" of the product) through the elimination of the fluorocarbon-based evaporative cooling agents and the use of increased amounts of the encapsulated evaporative cooling agents. More particularly, the effective life or wear-time of the product is improved by eliminating methyl perfluorobutyl ether and methyl perflouroisobutyl ether (i.e., the fluorocarbon-based evaporative cooling agents) from the formulations shown in Table 1 and increasing the proportions of sodium cocamidopropyl PG dimonium chloride phosphate, ethylhexyl isononanoate and isononyl isononanoate (i.e., the encapsulated evaporative cooling agents). The increased use of Structured Micelle Aggregates (SMA) such as sodium cocamidopropyl PG dimonium chloride phosphate, ethylhexyl isononanoate and isononyl isononanoate enhances the controlled and slow release of entrained solvents (e.g., water and/or alcohol). The controlled and slow evaporation of the entrained solvents provides makeup surface cooling over an extended period of time. Additionally, further cooling may be achieved by increasing the proportions of water, aloe barbandensis leaf extract, and methyl diisopropyl propionamide. Methyl diisopropyl propionamide may comprise from 0.001 to 2% of the formulation by weight.

More particularly, in one preferred form of the invention, the proportion of sodium cocamidopropyl PG dimonium chloride phosphate may comprise from 0.0001-3% of the formulation by weight, ethylhexyl isononanoate may comprise from 0.0001-3% of the formulation by weight and the proportion of isononyl isononanoate may comprise from 0.0001-3% of the formulation by weight.

Preferably, the proportion of sodium cocamidopropyl PG dimonium chloride phosphate comprises 0.085% of the formulation by weight, the proportion of ethylhexyl isononanoate comprises 0.17% of the formulation by weight and the proportion of isononyl isononanoate comprises 0.17% of the formulation by weight. Other components of the formulation may be adjusted as needed in order to compensate for the elimination of methyl perfluorobutyl ether and methyl perflouroisobutyl ether in the formulation and the increased proportions of sodium cocamidopropyl PG dimonium chloride phosphate, ethylhexyl isononanoate and isononyl isononanoate in the formulation.

Generally, the performance of the product is enhanced most (i.e., the cooling effect is greater) as the proportions of sodium cocamidopropyl PG dimonium chloride phosphate, ethylhexyl isononanoate and isononyl isononanoate are increased toward the higher ends of their proportional ranges. However, sodium cocamidopropyl PG dimonium chloride phosphate, ethylhexyl isononanoate and isononyl isononanoate are relatively expensive ingredients of the formulation, so as their proportions increase, the cost of manufacturing the product also increases.

The present invention provides extended cooling of the color cosmetics, which extends their useful life and improves the overall appearance of the color cosmetics. Among other things, the present invention provides longer wear, increased user comfort, reduced moisture loss, increased make-up surface luminosity, reduced surface shine, etc. In fact, the present invention provides a cosmetic formulation such that the make-up generally looks as good at the end of the day as it did at the beginning of the day.

In the foregoing description, the new formulation is described as being applied to the color cosmetics after the color cosmetics have been applied to the skin. Alternatively, and/or additionally, the novel formulation can also be applied to the skin prior to the application of the color cosmetics so as to extend the useful life of the color cosmetics.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

TABLE I

| Ingredient | Purpose | % by weight |
|---|---|---|
| WATER | solvent | 82.228 |
| ALCOHOL DENAT | solvent/antiseptic | 9 |
| POLYHYDROXYSTEARIC ACID | foam burst stabilizer | 2.23 |
| PVP | film former | 2 |
| METHYL PERFLUOROBUTYL ETHER | foam burst | 1.25 |
| METHYL PERFLUOROISOBUTYL ETHER | foam burst | 1.25 |
| DIMETHICONE PEG-7 PHOSPHATE | emulsifier for silicones, conditioned feeling on skin | 0.75 |
| PPG-3 BENZYL ETHER MYRISTATE | emollient, lubricant, high gloss, pigment wetting | 0.5 |
| CAPRYLYL GLYCOL | preservative | 0.5 |
| METHYL METHACRYLATE CROSS POLYMER | light diffusion, anti-shine, line reducer, oil absorber | 0.12 |
| SODIUM HYDROXIDE | PH Modifier | 0.07 |
| SODIUM COCAMIDOPROPYL PG DIMONIUM CHLORIDE PHOSPHATE | foam burst stabilizer | 0.05 |
| GLYCERETH-5 LACTATE | emollient, moisturizer | 0.01 |
| N,2,3-TRIMETHYL-2-ISOPROPYL BUTAMIDE | cooling agent | 0.01 |
| ETHYLHEXYL ISONONANOATE | dry feel emollient | 0.01 |
| ISONONYL ISONONANOATE | dry feel emollient | 0.01 |
| FRAGRANCE | | 0.01 |
| ALOE BARBANDENSIS LEAF EXTRACT | skin protectant, humectant, smoothing | 0.001 |
| POLOXAMER 407 | thickener | 0.001 |
| Totals | | 100 |

Note:
all of the foregoing percentage weights have a tolerance band of ±4% of their stated value and the absence of fluorocarbon-based evaporative cooling agents,
whereby the reduction of the surface temperature of the color cosmetics is achieved by a controlled release of the at least one entrained solvent by the encapsulated or suspended evaporative cooling agent.

2. The pumpable liquid spray formulation of claim 1 wherein sodium cocamidopropyl PG dimonium chloride phosphate comprises 0.085% by weight of the liquid spray formulation, ethylhexyl isononanoate comprises 0.17% by weight of the liquid spray formulation and isononyl isononanoate is 0.17% by weight of the pumpable liquid spray formulation.

3. The pumpable liquid spray formulation of claim 1 wherein the at least one encapsulant for evaporative cooling agent is polyhydroxystearic acid.

4. The pumpable liquid spray formulation of claim 3 wherein the polyhydroxystearic acid is 0.001%-3.0% (by weight) of the pumpable liquid spray formulation.

What is claimed is:

1. A pumpable liquid spray formulation for retarding degradation of color cosmetics, the pumpable liquid spray formulation being characterized by:
    the presence of encapsulated or suspended evaporative cooling agent wherein the encapsulated or suspended evaporative cooling agent comprises sodium cocamidopropyl PG dimonium chloride phosphate and ethylhexyl isononanoate and isononyl isononanoate wherein sodium cocamidopropyl PG dimonium chloride phosphate is between 0.0001-3% by weight of the pumpable liquid spray formulation and ethylhexyl isononanoate is between 0.0001-3% by weight of the pumpable liquid spray formulation and isononyl isononanoate is between 0.0001-3% by weight of the pumpable liquid spray formulation; and
    at least one entrained solvent wherein the at least one entrained solvent is selected from the group consisting of water, alcohol and mixture of alcohol and water;

5. The pumpable liquid spray formulation of claim 1 wherein the at least one entrained solvent is water.

6. The pumpable liquid spray formulation of claim 1 wherein the at least one entrained solvent component is alcohol.

7. The pumpable liquid spray formulation of claim 6 wherein the alcohol is between 0.2% and 14% by weight.

8. The pumpable liquid spray formulation of claim 1 wherein the at least one entrained solvent is a mixture of water and alcohol.

9. The pumpable liquid spray formulation of claim 8 wherein the formulation includes methyl diisopropyl propionamide.

10. The pumpable liquid spray formulation of claim 9 wherein the methyl diisopropyl propionamide comprises between 0.001% to 2% by weight.

11. The pumpable liquid spray formulation of claim 10 wherein the formulation further comprises micro-fine particulates to provide light diffusion whereby to make the skin appear less shiny or oily.

12. A method for improving cosmetic wear, the method comprising:

provide a pumpable liquid spray formulation for retarding degradation of color cosmetics, the pumpable liquid spray formulation being characterized by:

the presence of encapsulated evaporative cooling agent wherein the encapsulated or suspended evaporative cooling agent comprises sodium cocamidopropyl PG dimonium chloride phosphate and ethylhexyl isononanoate and isononyl isononanoate wherein sodium cocamidopropyl PG dimonium chloride phosphate is between 0.0001-3% by weight of the pumpable liquid spray formulation and ethylhexyl isononanoate is between 0.0001-3% by weight of the pumpable liquid spray formulation and isononyl isononanoate is between 0.0001-3% by weight of the pumpable liquid spray formulation; and at least one entrained solvent wherein the at least one entrained solvent is selected from the group consisting of water, alcohol and mixture of alcohol and water;

and the absence of fluorocarbon-based evaporative cooling agents, whereby the reduction of the surface temperature of the color cosmetics is achieved by a controlled and slow release of the at least one entrained solvent, by the encapsulated evaporative cooling agent;

applying color cosmetics to the skin of the user; and applying the pumpable liquid spray formulation to the color cosmetics, as a fine mist while the color cosmetics are on the skin of the user.

13. A method for improving cosmetic wear, the method comprising:

providing a pumpable liquid spray formulation for retarding degradation of color cosmetics, the pumpable liquid spray formulation being characterized by:

the presence of encapsulated evaporative cooling agent wherein the encapsulated or suspended evaporative cooling agent comprises sodium cocamidopropyl PG dimonium chloride phosphate and ethylhexyl isononanoate and isononyl isononanoate wherein sodium cocamidopropyl PG dimonium chloride phosphate is between 0.0001-3% by weight of the pumpable liquid spray formulation and ethylhexyl isononanoate is between 0.0001-3% by weight of the pumpable liquid spray formulation and isononyl isononanoate is between 0.0001-3% by weight of the pumpable liquid spray formulation; and at least one entrained solvent wherein the at least one entrained solvent is selected from the group consisting of water, alcohol and mixture of alcohol and water;

and the absence of fluorocarbon-based evaporative cooling agents, whereby the reduction of the surface temperature of the color cosmetics is achieved by a controlled release of the at least one entrained solvent, by the encapsulated evaporative cooling agent;

applying the pumpable liquid spray formulation to the skin of the user as a fine mist; and applying color cosmetics to the skin of the user over the pumpable liquid spray formulation.

14. A pumpable liquid spray formulation for retarding degradation of color cosmetics, the pumpable liquid spray formulation comprising a suspension, said suspension being characterized by:

the presence of evaporative cooling agent wherein the encapsulated or suspended evaporative cooling agent comprises sodium cocamidopropyl PG dimonium chloride phosphate and ethylhexyl isononanoate and isononyl isononanoate wherein sodium cocamidopropyl PG dimonium chloride phosphate is between 0.0001-3% by weight of the pumpable liquid spray formulation and ethylhexyl isononanoate is between 0.0001-3% by weight of the pumpable liquid spray formulation and isononyl isononanoate is between 0.0001-3% by weight of the pumpable liquid spray formulation; and at least one entrained solvent wherein the at least one entrained solvent is selected from the group consisting of water, alcohol and mixture of alcohol and water;

and the absence of fluorocarbon-based evaporative cooling agents, whereby the reduction of the surface temperature of the color cosmetics is achieved by a controlled release of the at least one entrained solvent, by the evaporative cooling agent.

* * * * *